United States Patent [19]
Beuret

[11] Patent Number: 5,190,600
[45] Date of Patent: Mar. 2, 1993

[54] METHOD OF MONITORING A HEAT TREATMENT WITH CARBON PENETRATION

[76] Inventor: Pierre Beuret, Route de Bure 21, 2900 Porrentruy, Switzerland

[21] Appl. No.: 745,710

[22] Filed: Aug. 16, 1991

Related U.S. Application Data

[62] Division of Ser. No. 527,319, May 23, 1990, Pat. No. 5,064,620.

[30] Foreign Application Priority Data

Jun. 1, 1989 [CH] Switzerland ............... 2059/89

[51] Int. Cl.⁵ ..................... C21B 7/24; C21D 11/00
[52] U.S. Cl. ........................ 148/509; 266/81
[58] Field of Search .............. 266/80, 81; 148/508, 148/507; 422/95, 98

[56] References Cited

U.S. PATENT DOCUMENTS 2,811,037 10/1957 Beard .................................. 266/80
3,011,873 12/1961 Davis, II .............................. 148/508

*Primary Examiner*—Scott Kastler
*Attorney, Agent, or Firm*—Oliff & Berridge

[57] ABSTRACT

A probe (14) comprises a tubular electrical conductor (15) supported by a sleeve of insulating material (16). The two ends of the conductor are connected to couplings (23, 24) for the circulation of a reducing gas through the entire length of the conductor, as well as to an electric circuit (20) kept at a constant voltage and hence permitting measurement of the resistance in a segment (15c) of the conductor which is exposed to the atmosphere of a furnace, the resistivity of the segment varying as a function of the carbon content of the wall of the conductor.

7 Claims, 5 Drawing Sheets

ATMOSPHERE OF FURNACE
GAS :   $CH_4 - CO - CO_2 - H_2 - N_2 - H_2O$

METHOD OF MONITORING A HEAT TREATMENT WITH CARBON PENETRATION

This is a Division of application Ser. No. 07/527,319 filed May 23, 1990, now U.S. Pat. No. 5,064,620.

BACKGROUND OF THE INVENTION

1. Technical Field

This invention relates to case-hardening technology, and more particularly to a method of monitoring a heat treatment with carbon penetration, carried out on workpieces placed in a furnace, of the type comprising the use of a probe for measuring the electrical resistance of a conductor placed in the presence of the atmosphere of the furnace, and the processing of the resistance values successively obtained by these measurements. The invention further relates to a probe for carrying out this method.

2. Description of the Related Art

The various developments which have taken place during the past few years in the art of gaseous cementation have pertained essentially to reducing the cycle times, to the quality and reproducibility of the treatments, as well as to the gas consumption and improvement of the safety conditions.

This research has led to supersaturating atmospheres, often out of equilibrium, maintained in agitated reactors, used at atmospheric pressure or under partial pressure of hydrocarbons in a vacuum furnace.

The values of the carbon potential carried out by indirect measurement, based on residual gases such as $H_2O$, $CO_2$, or $O_2$, can no longer be validly defined.

In treatment under vacuum or in a supersaturating atmosphere, where the release of the carbon does not take place via cracking of the CO molecule but by the direct decomposition of a hydrocarbon, the concept of equilibrium potential no longer exists and could be replaced by the term "kinetic potential," i.e., enrichment according to a linear law (in the usual range of cementation) as a function of time.

A method of monitoring and regulating completely adapted for following these reactions is the direct measurement of the carbon flux.

The principle consists in following in real time the carbon which enters at the surface of the measuring element, either by weighing (thermobalance or strip system) or by gas analysis after secondary reaction of the carbon with a gas in an system isolated from the reactor, or by measurement of the resistance of a detector as a function of its carbon enrichment.

The first principle, based on weighing an element, can hardly be used in an industrial reactor, for the electronic balance is very sensitive to jolts and vibrations. As for measurement on foil, the values are only intermittent and indicative of a state during a brief period of time.

The second method, devised by Meyer and Schmidt, consists in using a carbon-flux probe in which the carbon diffuses from the atmosphere of the furnace into a thin-walled steel tube; a decarburizing atmosphere based on humid $N_2$ and $H_2$ circulates within the tube. The carbon flux is determined from the $CO/CO_2$ content of this atmosphere (see U.S. Pat. No. 3,843,419, for example).

The main drawback of this system is that the analysis does not take place in situ, and the measurement chain based on infrared analyzers becomes complex and inaccurate.

The other system, developed by Jochen Wünning, uses the resistance method: a detector in the form of a very fine, short wire is enriched in the atmosphere of the furnace, and the measurement of its electrical resistance gives an indication of its carbon content, hence of the carbon flux as a function of time. At regular intervals, the probe is decarburized by an injection of $H_2$, $H_2O$, and $N_2$ around the detector (J. Wünning, Die C-Stromregelung bei der Gasaufkohlung, HTM 40, 1985).

This technique cannot be used in a vacuum reactor, for the introduction of a decarburizing gas shifts the gaseous reactions, weakens the enrichment kinetics, causes intergranular oxidation at the surface of the workpieces, and increases the working pressure.

The fragility of the wire and the complexity of its assembly after breakage (for soldering) must likewise be noted.

U.S Pat. No. 2,935,866 to Schmidt and Wünning also describes a method of measurement using the electrical resistance of conductors. In this case, one detector is placed in an atmosphere having a known carbon content and another in the atmosphere to be measured.

SUMMARY OF THE INVENTION

It is an object of this invention to provide an improved method and probe which eliminate these drawbacks.

To this end, in the method according to the present invention, of the type initially mentioned, a tubular-shaped conductor is used, one of the faces of a segment of the conductor is placed in contact with the atmosphere of the furnace, and the space adjoining the other face of the segment is connected to a supply of reducing gas.

The probe according to the present invention comprises a U-shaped tubular detector made of a ferrous metal, the two ends of which pass through a core of insulating material and are connected electrically to a voltage source by a connection which passes through an instrument for measuring electrical resistance, on the one hand, and, from the point of view of the flow of the fluids, to a feed supply and to an exhaust of reducing gas, on the other hand.

The principle of this invention consists in using a tubular detector in which there circulates a decarburizing atmosphere on the basis of $N_2$, $H_2$, $H_2O$, and $CO_2$. This tube being placed partially in the atmosphere of the furnace, and its wall being very thin, the carbon diffuses through and combines with the $H_2O$ to be exhausted from the system.

The carbon flux is measured by the variation in resistivity of the detector. Knowing the rate of gas flow and the length and surface of the detector, the measurement of this resistance permits a continuous analysis, and the advantages are numerous:

the possibility of working in vacuum reactors and in an oxidizing-reducing gas atmosphere;

a continuous and precise method of analysis, for it is carried out in the reactor;

easy interchangeability (by electrodes);

reliability and flexibility of use;

analysis based on an electric signal without processing making use of infrared means;

convenient control of an installation based on this system;

rapid response time.

BRIEF DESCRIPTION OF THE DRAWINGS

Preferred embodiments of the inventive method and probe will now be described in detail with reference to the accompanying drawings, in which:

FIGS. 1 and 2 illustrate the aforementioned prior art method developed by Wünning for monitoring a cementation heat treatment. A probe 1 within an envelope 2 passing through the wall 3 of a furnace comprises a U-shaped ferrous metal wire 4, the bend of which constitutes a resistor 5. Probe 1 further comprises a temperature-measurement thermocouple 6. A calculating unit 7 is designed to control the sending of a current across resistor 5, to measure periodically the value of the resistance, to control as well, by means of a valve 8, a feed of decarburizing gas in the space within envelope 2, and finally to control by means of a valve 9 the flow of cementation gas entering the furnace.

Figure 1:
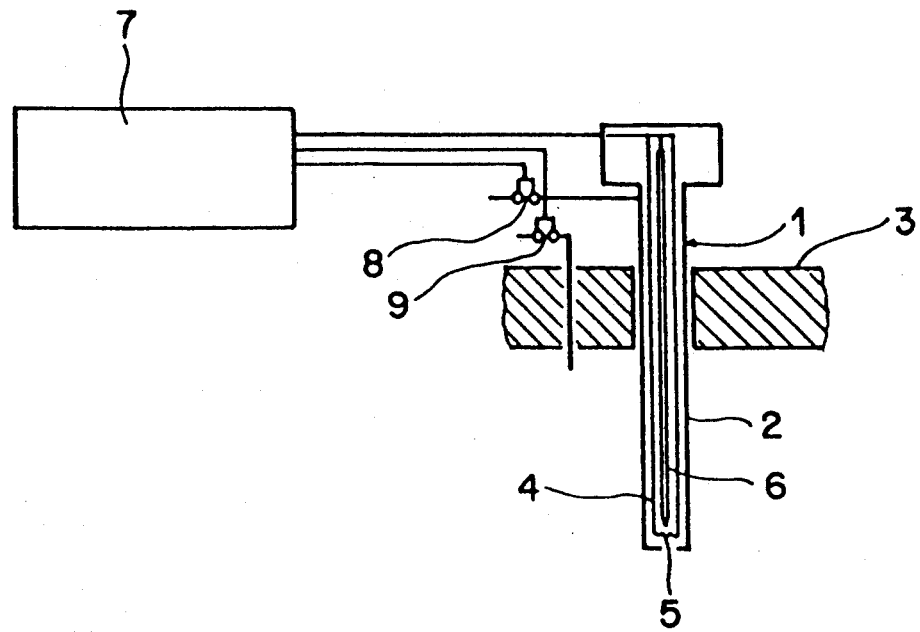
FIG. 1 is a diagram of a prior art probe.
Figure 2:
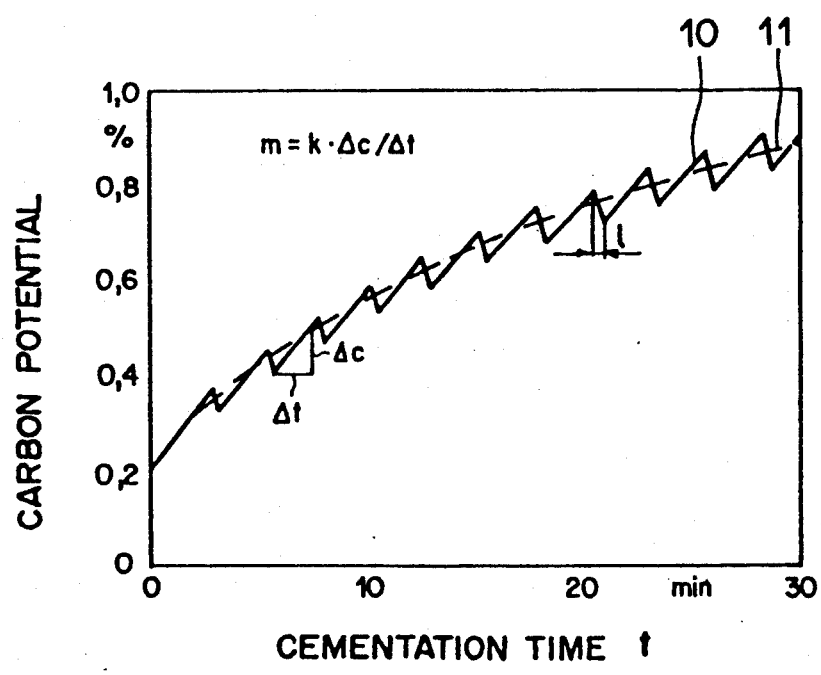
FIG. 2 is a graph illustrating the operation of the probe of FIG. 1.

For carrying out this process, a calculation program based upon the resistance values measured on segment 5 of wire 4 was developed. As this segment of wire, placed in the furnace, has a tendency to become rapidly saturated with carbon, whereas the carbon content of the surface zone of the workpieces to be case-hardened increases gradually as the carbon diffuses to the interior of the workpieces, the prior art method consists in decarburizing wire 4 periodically, so that the carbon content of this wire, as a function of time, yields a zigzag curve 10 (FIG. 2), whereas the carbon content of the surface zone of the workpieces yields a continuous curve 11. The intervals during which decarburization is carried out are designated as "1" in FIG. 2.

As may be seen, the decarburization of wire 4 necessitates the introduction of the decarburizing gas within the furnace, so that this technique cannot be used in a vacuum reactor and presents drawbacks even when the atmosphere of the furnace has pressure.

Figure 3:
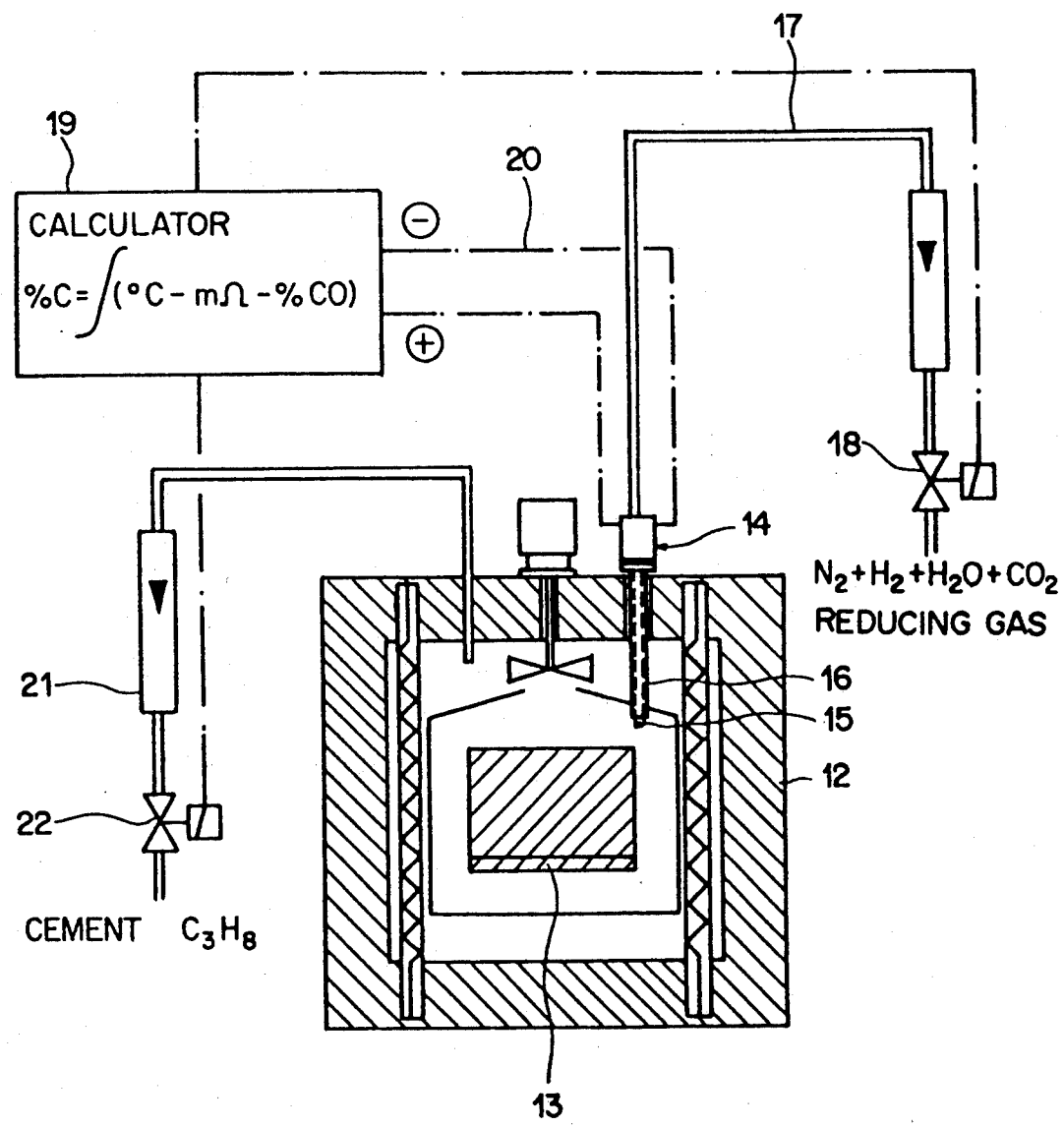
FIG. 3 is a diagram, partly in section, of a furnace equipped with a probe according to the present invention for carrying out the inventive method.

FIG. 3 therefore illustrates in a general way the arrangement by means of which the method to be described below may be carried out. A furnace 12 contains a charge 13 of workpieces to be case-hardened. A probe 14 comprises a detector in the form of a U-shaped tubular electrical conductor 15 disposed within a support sleeve 16. The two ends of tubular conductor 15 are connected to feed and exhaust pipes 17 so that a reducing gas can circulate within the conductor. This circulation is controlled by one or more valves 18, which are in turn controlled from a control unit 19. The circulation of an electric current in tubular conductor 15 via a circuit 20, and the measurement of the electrical resistance of conductor 15, are also effected by control unit 19.

A feed device 21, controlled by a valve 22, allows the cementation gas to be introduced into furnace 12.

Figure 4:
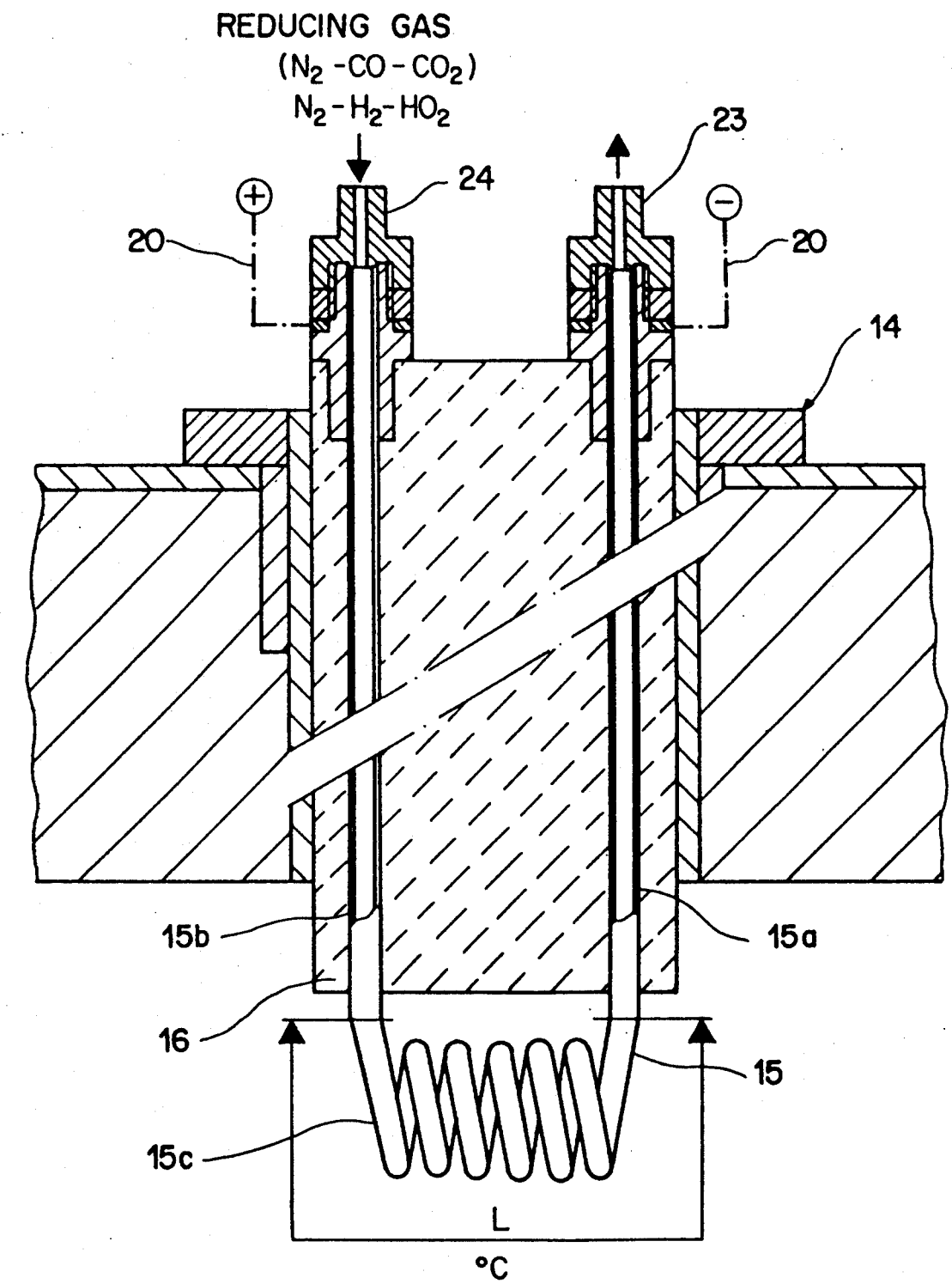
FIG. 4 is a section on a larger scale of the probe shown in FIG. 3.

FIG. 4 shows the structure of probe 14 in more detail. Tubular conductor 15 comprises two arms 15a and 15b which extend parallel to the inside of sleeve 16, the latter being a part serving as a support, as electrical and thermal insulation, and as protection for conductor 15. A short segment 15c of conductor 15, of a length L, is exposed to the atmosphere of the furnace and constitutes the detector proper. In the embodiment being described, segment 15c is coiled in the shape of a solenoid. It might also be disposed along a serpentine line or any other layout offering a large surface in contact with the atmosphere of the furnace together with compactness and unobstructed circulation. The metal of which conductor 15 is made is a ferrous metal of a composition such that measurement of its electrical resistance makes it possible to determine the average carbon content in the thickness of the conductor wall. This wall will be thin enough, e.g., about 0.1 mm, so that the carbon may diffuse rapidly through it and a state of dynamic equilibrium be easily brought about, as will be seen below.

Arms 15a and 15b of tubular conductor 15 are preferably copper-coated on the outside in order to reduce to a minimum the drop in voltage and the modification of resistance between the ends of the two arms 15a and 15b and segment 15c. These two ends are, in fact, connected outside the furnace both to couplings 23 and 24 leading to reducing-gas circuit 17, and electrically to circuit 20.

Figure 5:
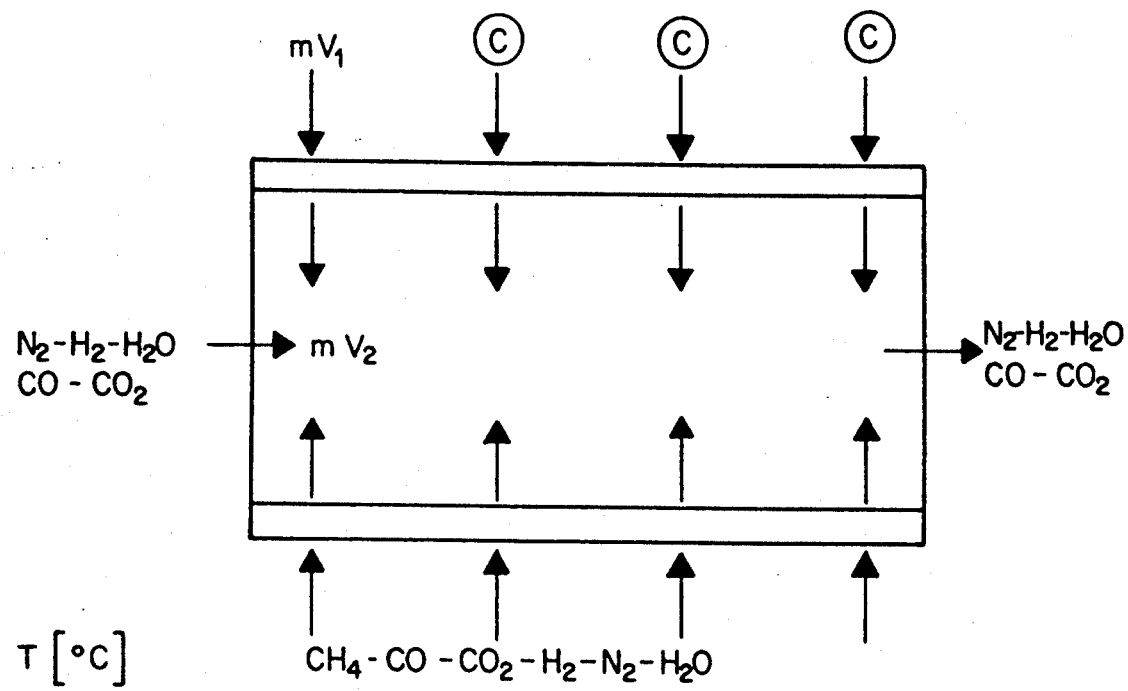
FIG. 5 is a sectional diagram on a still larger scale for explaining the course of the method, showing a segment of the tubular conductor visible in FIG. 4.
Figure 6:
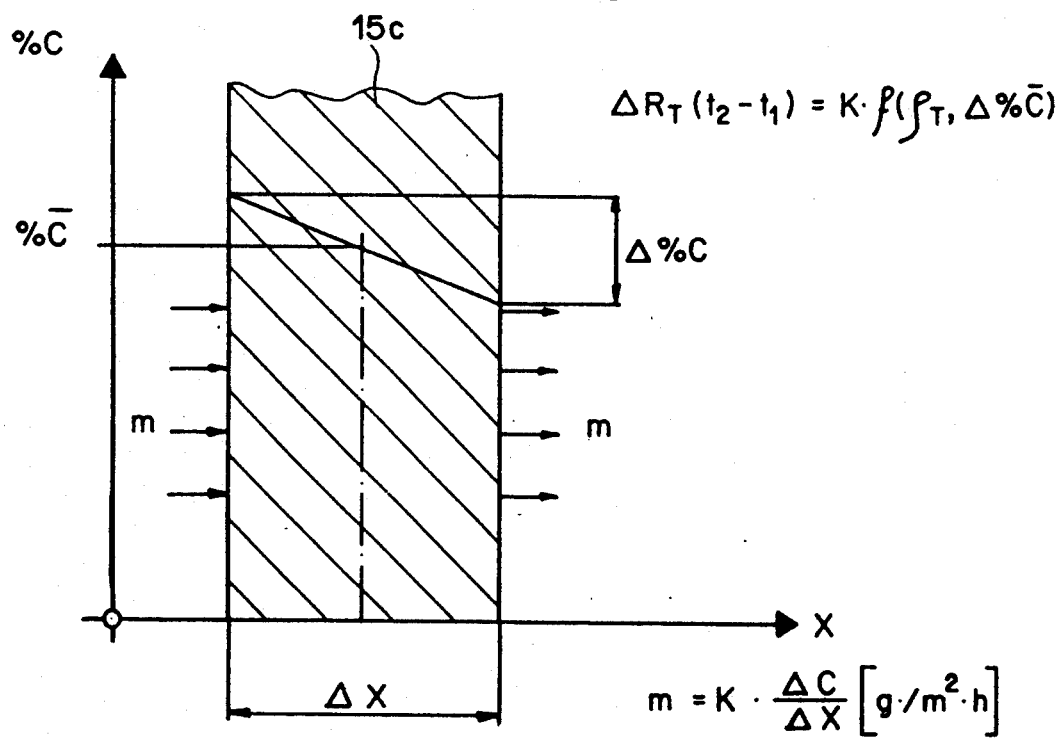
FIG. 6 is a diagrammatic view showing in section a segment of the wall of the tubular conductor, and FIG. 7 a graph showing the evolution of the carbon content in the surface zone of the workpieces placed in the furnace of FIG. 3.

The method described may be carried out during the cementation operation either continuously or intermittently. FIGS. 5 and 6 illustrate the phenomenon to be monitored and give the physical magnitudes whose values are to be processed by the computer. FIG. 5 shows a short tubular segment representing a portion of conductor 15 with its thin cylindrical wall. If the outside surface of this tubular segment is exposed to a carburizing atmosphere at a given temperature T, the carbon penetrates into the metal of the conductor, and the quantity of carbon brought in is represented by the term $mV_1$. This carbon diffuses through the wall; and as the interior space of the tubular conductor is in the presence of a reducing gas which circulates along the length of the conductor, this gas exhausts the carbon, the quantity of carbon exhausted being represented by the term $mV_2$.

FIG. 6 illustrates the situation of equilibrium which is thus established. On the graph, the carbon content is given on the y-axis and the distance through the wall of conductor 15c on the x-axis. The carbon content on the outside surface of this wall is greater than on its inside surface, and the difference $\Delta \%C$ corresponds to a transfer of mass of carbon m (in grams per sq.m. per hour).

Figure 7:
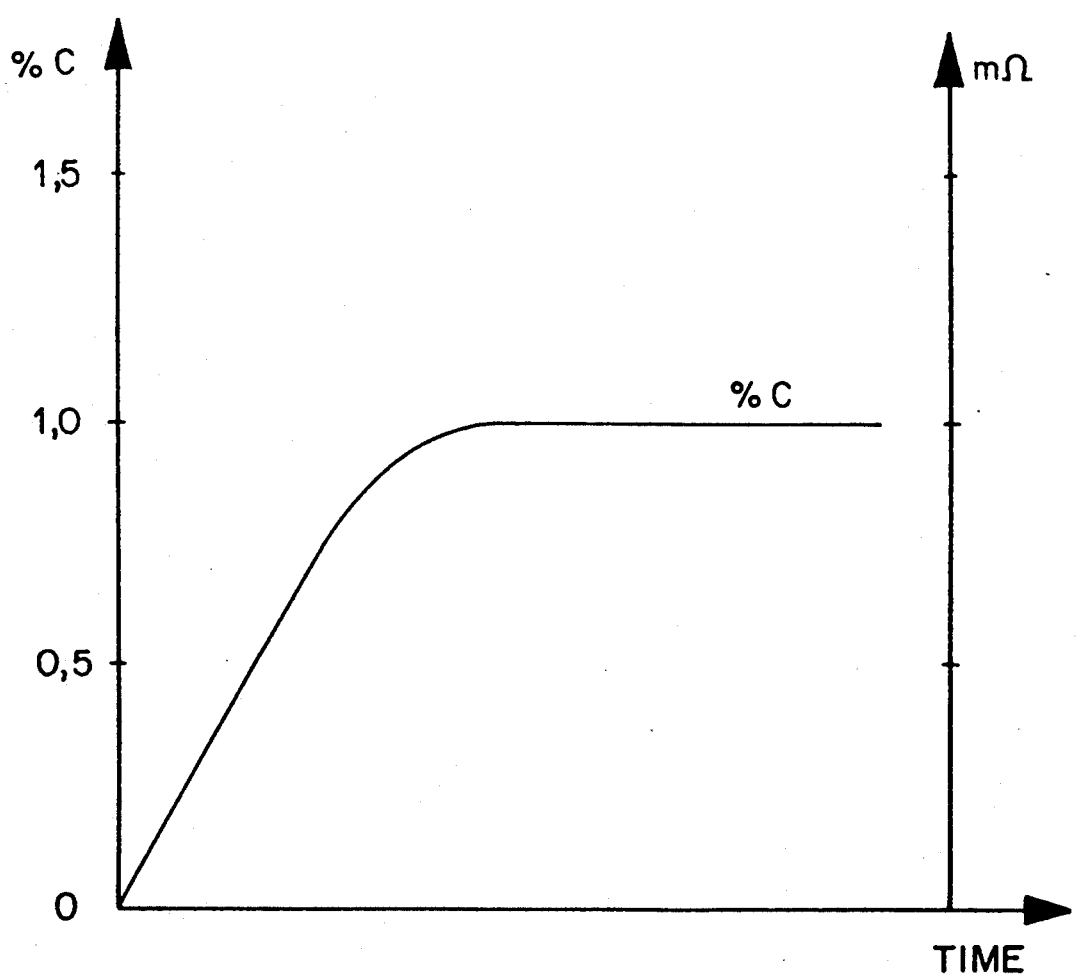

The value of the resistance of conductor segment 15c depends upon temperature T, length L, thickness $\Delta X$, and the coefficient of resistivity, which in turn depends upon the carbon content. Thus the value of the resistance at any given moment t makes it possible to determine at that moment the average carbon content $\%C$ in conductor wall 15c and the evolution of that value in the course of time, taking into account the rates of flow of carburizing gas and of reducing gas $mV_1$ and $mV_2$. It permits determining the degree of evolution of the phenomenon of penetration of carbon into the workpieces and, consequently, to follow their carburization as shown in FIG. 7.

When the conditions of equilibrium are achieved, the interior space of the tube comprises a constant carbon potential. A constant flux of carbon is absorbed by the constant flow of the reducing gas.

What is claimed is:

1. A method of monitoring a heat treatment with carbon penetration, carried out on workpieces placed in a furnace, comprising the use of a probe for measuring the electrical resistance of a conductor placed in the presence of the atmosphere of the furnace, and the processing of the resistance values successively obtained by such measurements, wherein the improvement comprises the steps of:

using a tubular conductor, placing one of the faces of a segment of the conductor in contact with the atmosphere of the furnace, and connecting the space adjoining the other face of the segment to a supply of reducing gas.

2. The method of claim 1, wherein the wall of said segment is made thin enough to achieve a state of dynamic equilibrium within a predetermined time, the carbon diffusing through the wall and being exhausted by the reducing gas.

3. The method of claim 1, comprising the steps of placing the outside face of the tubular conductor in the presence of the atmosphere of the furnace and connecting the interior of the tubular conductor to the supply of gas.

4. The method of claim 3, wherein the wall of said segment is made thin enough to achieve a state of dynamic equilibrium within a predetermined time, the carbon diffusing through the wall and being exhausted by the reducing gas.

5. The method of claim 1, wherein a mixture containing $N_2$ and at least one of the components taken from the group consisting of $H_2$, $H_2O$, and $CO_2$ is used as the reducing gas.

6. The method of claim 1, this method being carried out continuously, wherein decarburization of the conductor by a regulated flow of reducing gas is carried out continuously.

7. The method of claim 1, this method being carried out cyclically, wherein a flow of reducing gas is controlled for effecting decarburization of the wall of the tubular conductor during intermittent periods of limited duration.

* * * * *